United States Patent [19]
Lewis et al.

[11] Patent Number: 5,814,275
[45] Date of Patent: Sep. 29, 1998

[54] OBSTRUCTION DETECTOR FOR A FLUID FLOW LINE OF A MEDICAL LABORATORY INSTRUMENT

[75] Inventors: Gregory D. Lewis, Raleigh; Dean Keiter, Durham; Mario Moreno, Raleigh, all of N.C.

[73] Assignee: Akzo Nobel N.V., Arnhem, Netherlands

[21] Appl. No.: 693,275

[22] PCT Filed: Feb. 15, 1995

[86] PCT No.: PCT/US95/02014

§ 371 Date: Dec. 12, 1996

§ 102(e) Date: Dec. 12, 1996

[87] PCT Pub. No.: WO95/22753

PCT Pub. Date: Aug. 24, 1995

[51] Int. Cl.$^6$ ...................................................... G01N 1/14
[52] U.S. Cl. .......................... 422/63; 422/100; 436/54; 436/180; 73/37; 73/864.11
[58] Field of Search .................. 422/63, 67, 81, 422/100, 104, 112; 436/43, 49, 50, 54, 174, 180; 73/37, 863.01, 864.11; 340/626

[56] References Cited

U.S. PATENT DOCUMENTS

| | | |
|---|---|---|
| 3,848,962 | 11/1974 | Nelson ........................................ 350/86 |
| 4,430,886 | 2/1984 | Rood . |
| 4,554,927 | 11/1985 | Fussell ..................................... 128/670 |
| 4,559,034 | 12/1985 | Kirita . |
| 4,683,654 | 8/1987 | Scholten et al. ........................... 29/832 |
| 4,807,984 | 2/1989 | Kurimura et al. ....................... 350/529 |
| 4,976,155 | 12/1990 | Challandes . |
| 5,026,348 | 6/1991 | Venegas . |
| 5,081,045 | 1/1992 | McGill . |
| 5,121,658 | 6/1992 | Lew . |
| 5,236,666 | 8/1993 | Hulette et al. . |
| 5,330,717 | 7/1994 | Berteloot et al. . |
| 5,463,895 | 11/1995 | Brentz .................................... 73/61.71 |
| 5,488,854 | 2/1996 | Kawanabe et al. .................... 73/19.05 |
| 5,525,298 | 6/1996 | Anami ...................................... 422/63 |
| 5,537,880 | 7/1996 | Takeda et al. ....................... 73/864.25 |
| 5,540,081 | 7/1996 | Takeda et al. ............................. 73/37 |

Primary Examiner—Long V. Le
Attorney, Agent, or Firm—Gregory R. Muir

[57] ABSTRACT

An apparatus for detecting obstructions of a flow line. A detector housing is provided having a cavity therein. The detector housing has first and second openings into the cavity. The flow line is attached to the detector housing establishing a flow path through the first opening, the cavity, and the second opening, respectively. A pressure detector detects changes in pressure within the cavity, indicating the presence of an obstruction.

11 Claims, 8 Drawing Sheets

OBSTRUCTION DETECTOR FOR A FLUID FLOW LINE OF A MEDICAL LABORATORY INSTRUMENT

BACKGROUND OF THE INVENTION

The present invention relates to an apparatus for detecting obstructions of a flow line, in particular, the fluid flow line of a medical instrument.

Automated sample handling systems are known that automatically aspirate patient fluid samples, such as blood plasma, from sample tubes for subsequent monitoring or testing of the fluid sample. For example, in U.S. Pat. No. 5,236,666 to Hulette et al., entitled "Temperature Regulation in a Sample Handling System for an Optical Monitoring System," there is disclosed an automated sample handling system for an optical evaluation instrument that can handle a high throughput of patient samples with a high degree of versatility, adaptability, and reliability. Hulette et al. discloses a sample handling system which allows walk-away automation once sample tubes containing patient samples are loaded into the system. The sample tube is automatically advanced to a piercer where a piercing probe is caused to pierce the septum of the sample tube. A sample probe is lowered a predetermined distance into the tube to aspirate a programmed amount of sample. The sample probe is then removed from the sample tube and the sample subsequently dispensed into a cuvette.

Typically, the amount of fluid sample aspirated with automated sampling handling systems is relatively small for example, 105 to 500 microliters. Precise aspiration of the sample from the sample tube is therefore critical. Due to the micro-amounts of fluid being aspirated, relatively small obstructions within the fluid sample, such as blood clots, can prevent the requisite amount of fluid from being drawn from the sample tube, resulting in inaccurate test results and decreasing the overall efficiency of the system.

Precision microfluid pumps, such as Cavro brand pump, manufactured by Cavro Scientific Instruments, Incorporated of Sunnyvale, Calif., have been developed that can accurately aspirate and dispense the aforementioned quantities. The Cavro brand pump is provided with a syringe having a plunger, and a stepper motor. To obtain the necessary precise volumetric delivery, the stepper motor moves the plunger a certain distance, for example, 0.0001 inch, aspirating an amount of fluid proportional to the distance moved.

When a pump begins a normal aspiration cycle, there is associated with this cycle within the fluid flow line an initial vacuum and a subsequent increase in pressure. When the pump, for example, the aforementioned Cavro brand pump, is turned on, the plunger within the pump is moved and begins drawing a vacuum. As fluid is drawn into the fluid flow line, the fluid continues to move until the plunger of the pump stops. Because a fluid in motion tends to stay in motion, when the moving fluid hits an immovable object, such as the piston, there is a resultant sudden pressure increase. However, if an obstruction, such as a blood clot, prevents the flow of the fluid within the flow line, this increase of pressure is absent.

In the past, an operator or technician would typically manually check the sample tube for obstructions by holding the sample tube up to the light and swishing the contents around while searching for foreign material. However, this method requires human intervention, diminishing the automation and flexibility of the aforementioned automated systems. Therefore, an automated device for detecting obstructions within a fluid flow line, minimizing human intervention, is desired.

The inventors experimented with an automated system of detecting obstructions in the fluid flow lines utilizing commercially available pressure detectors placed within the flow line of the medical instrument, in between the aspirating probe and the corresponding pump. If a pressure increase at the end of the aspiration cycle was not detected, this would indicate an obstruction of the fluid flow line, allowing the appropriate action to be taken. Stated alternatively, by monitoring the pressure signal associated with the fluid flow line, the presence or lack thereof of an obstruction could be determined.

It was discovered that the commercially available pressure detectors were either too delicate or lacked the sensitivity for this application. The instantaneous pressures that were developed due to the pumping action of the microfluid pumps often exceeded the burst pressure of the commercially available pressure sensors, causing them to break or malfunction.

SUMMARY OF THE INVENTION

It is an object of the present invention to avoid the aforementioned drawbacks by the provision of an obstruction detector having a durable, leak-proof housing through which the fluid sample flows.

It is a further object of the invention to provide the obstruction detector with a reliable pressure sensor not subject to malfunction due to pressure extremes for monitoring the pressure changes occurring within the housing.

It is yet another objective of the present invention to provide the detector housing with an internal cavity that prevents the accumulation of bubbles within the detector.

The above and other objects are accomplished according to the invention by the provision of an apparatus for detecting obstructions of a flow line including: a detector housing having a cavity therein, the detector housing having first and second openings into the cavity; means for attaching the flow line to the detector housing whereby a flow path is established through the first opening, the cavity, and the second opening, respectively; and pressure detection means for detecting changes in pressure within the cavity.

The invention will be described below in greater detail in connection with embodiments thereof that are illustrated in the drawing figures, where like reference numerals identify corresponding components.

DETAILED DESCRIPTION OF THE INVENTION

Figure 1:
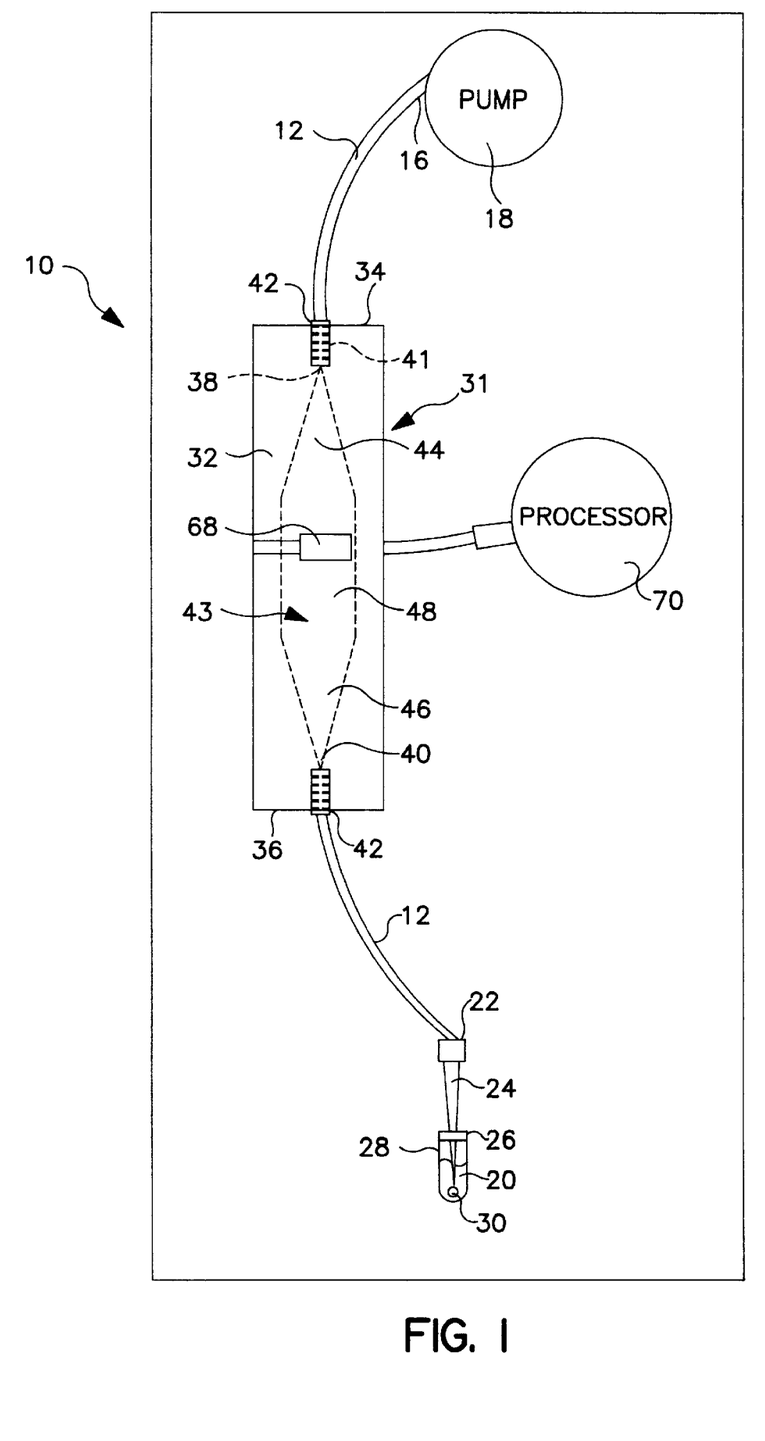
FIG. 1 is an axial elevation, showing internal structure in hidden lines, of the present invention attached within a fluid flow line of a medical laboratory instrument.

Referring to FIG. 1, a medical laboratory instrument 10 having a fluid flow line 12 is illustrated. Medical laboratory instrument 10 may be, for example, an automated sample handling device such as disclosed in U.S. Pat. No. 5,236,666 discussed above. Attached to one end 16 of fluid flow line 12 is a precision microfluid pump 18 such as a Cavro brand pump, manufactured by Cavro Scientific Instruments, Incorporated of Sunnyvale, California, that can accurately aspirate and dispense precision quantities of a fluid sample 20. Attached to the other end 22 of fluid flow line 12 is a piercing probe 24. Piercing probe 24 is caused to pierce the septum 26 of the sample tube 28 so that a programmed amount of fluid sample 20 contained within sample tube 28 can be withdrawn.

Due to the micro-amounts of fluid being aspirated, relatively small obstructions 30, such as blood clots, can prevent the requisite amount of fluid from being drawn from sample tube 28, resulting in inaccurate test results and decreasing the overall efficiency of the system.

To detect obstructions 30, an obstruction detector 31 is placed within fluid flow line 12 between ends 16 and 22. Obstruction detector 31 includes a detector housing 32. Preferably, detector housing 32 has an essentially symmetrical, cylindrical shape, including a first end 34 and an oppositely located second end 36. Each end 34, 36 is further provided with a concentric threaded female connector 41 for attaching fluid flow line 12 to detector housing 32. Female connectors 41 have respective, essentially concentric openings 38, 40, typically having a 0.05 inch diameter. Fluid flow line 12 is severed and provided with a male flow line connector 42 at each severed end. Each male connector 42 is connected to a respective female connector 41 of detector housing 32, thus establishing a fluid flow path from piercing probe 24, through detector housing 32, to pump 18.

Within detector housing 32 and between ends 34 and 36 is a cavity 43. Typically, cavity 43 has a first conically tapered region 44 adjacent to opening 38, a second conically tapered region 46 adjacent to opening 40, and a cylindrically shaped region 48 therebetween. Each tapered region tapers outward towards cylindrically shaped region 48, for example, at an angle of inclination of about 23 degrees. It has been discovered that if the angle of inclination is too steep, then micro bubbles flowing through fluid flow line 12 will attach themselves to the sloped tapered region. Such bubbles tend to expand and contract with pressure fluctuations, interfering with the precision and accuracy of the system.

Typically, the diameter at the apex of each conically tapered region corresponds to the diameter of the respective opening 38, 40, and the base diameter of each conically tapered region corresponds to the diameter of cylindrically shaped region 48, preferably 0.5 inch. Openings 38, 40 and cavity 43 establish a continuation of the flow path of fluid flow line 12.

Figure 2:
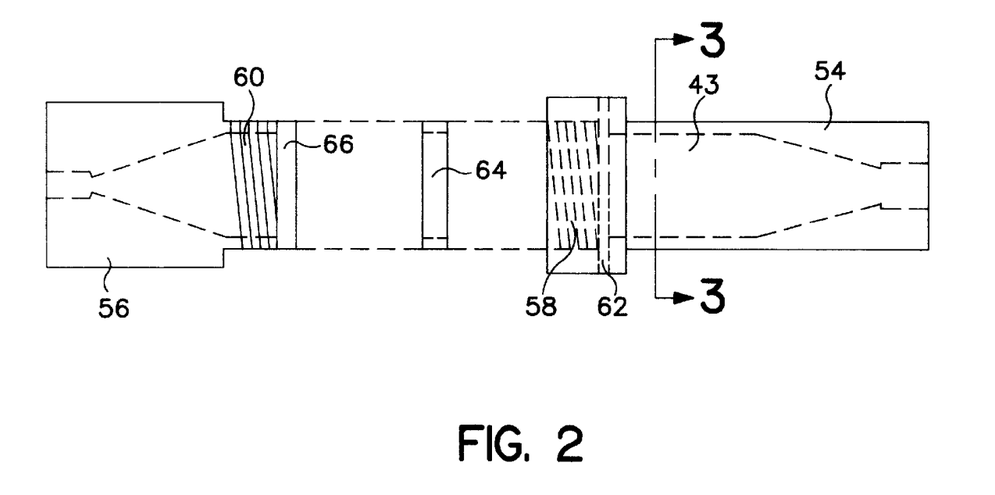
FIG. 2 is an exploded plan view of the detector housing, and the sealing ring.
Figure 3:
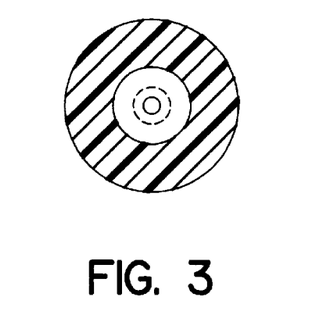
FIG. 3 is a cross-sectional view of the detector housing along sectional line 3-3 of FIG. 2.

As illustrated in FIGS. 2 and 3, preferably detector housing 32 comprises a first and a second portion 54, 56 connectable to each other in an area corresponding to cavity 43. First portion 54 is provided with a concentric threaded female connection 58, and second portion 56 is provided with a corresponding threaded male connection 60. First portion 54 has a concentric o-ring groove 62 for receiving an o-ring 64 located at a base of female connection 58. Male connection 60 has a raised boss 66 for contact with o-ring 64 when first and second portions 54, 56 are threaded together. It has been discovered that the aforementioned arrangement results in a leak-proof detector housing that can be economically manufactured. Further, the placement of oring 64 and raised boss 66 prevents the entrapment of air within the threaded connection and the assembled detector housing.

Referring back to FIG. 1, a pressure detector 68 is provided for detecting changes in pressure within cavity 43. Preferably, pressure detector 68 comprises a piezo-electric tape, for example, Kynar Brand piezo-electric tape, manufactured by Flexible Film Products Group, a division of Amp Industries in Valley Forge, Pa., wrapped around the exterior of detector housing 32 in an area corresponding to cavity 43. Pressure detector 68 transmits a signal corresponding to the rate of change in the pressure within cavity 43 to a processor 70.

Typical operation of obstruction detector 31 in a medical laboratory instrument 10, such as the automated sample handling system disclosed in U.S. Pat. No. 5,236,666, is as follows.

Piezo-electric tape 68 is electrically connected to processor 70. Obstruction detector 31 is placed between pump 18 and piercing probe 24 with the appropriate flow line connections being made, thus establishing a fluid flow path from pump 18, through first opening 38, cavity 43 and second opening 40, to piercing probe 24. Typically, to eliminate air, fluid flow line 12 and obstruction detector 31 are primed with a liquid, such as a wash buffer (not shown).

The sample tube septum 26 is pierced by piercing probe 24, beginning the aspiration cycle. The typical aspiration cycle causes an initial vacuum and a subsequent increase in pressure within fluid flow line 12. When pump 18, for example, the aforementioned Cavro pump, is turned on, a plunger (not shown) within the pump is moved and begins drawing a vacuum. As fluid is drawn into fluid flow line 12, the fluid continues to move until the plunger of the pump stops. Because a fluid in motion tends to stay in motion due to inertia, when the moving fluid hits an immovable object, such as the pump piston, there is a resultant sudden pressure increase. However, if an obstruction, such as a blood clot, prevents the flow of the fluid within the flow line, this increase in pressure is absent. By monitoring the pressure within the fluid flow path, the presence or lack thereof of obstruction 30 can be determined, allowing the appropriate action to be taken.

Typically, pressure detector 68 is a piezo-electric tape wrapped around the full circumference of detector housing 32 in an area corresponding to cylindrical shaped region 48 of cavity 43. The piezo-electric tape measures the microstrain of the detector housing, i.e., the expansion and contraction of the housing associated with pressure fluctuations occurring within cavity 43. Thus, because the sensitivity of the pressure detector is proportional to the amount of sensor area, by increasing the diameter of cavity 43 in cylindrical shaped region 48, the sensitivity of the pressure detector is likewise increased.

Figure 4:
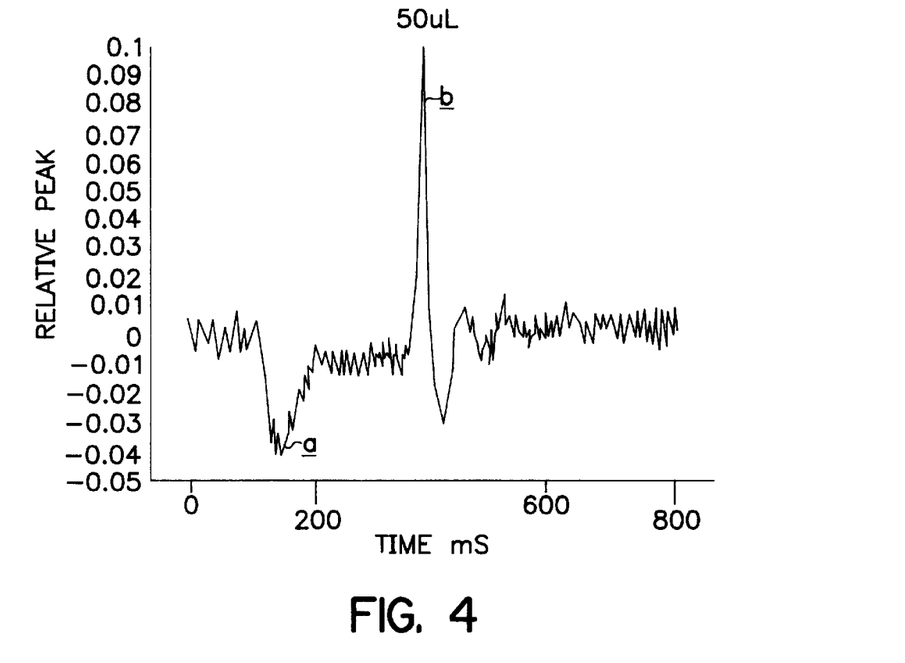
FIG. 4 is a graphical representation of a normal aspiration cycle of a fluid, illustrating a vacuum spike and a pressure pulse.
Figure 5:
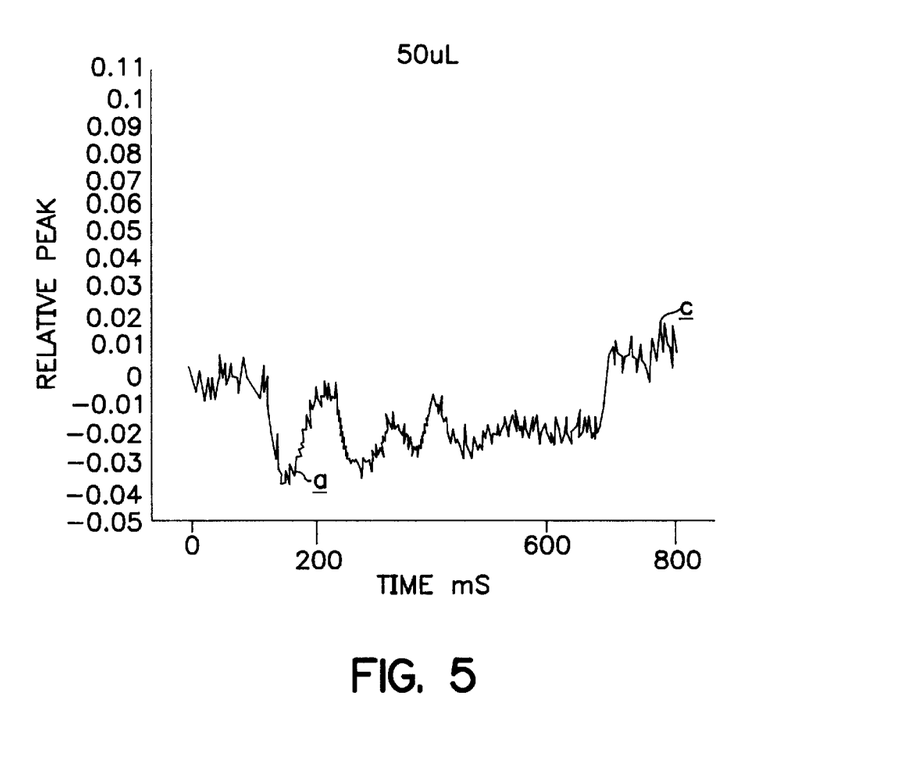
FIG. 5 is a graphical representation of an aspiration cycle of a fluid having an obstruction.

The measured microstrain corresponds directly to the time rate of change of the pressure within detector housing 32, i.e.

the derivative of the actual pressure. As illustrated in FIG. 4, when there is no obstruction 30 present, there is a distinct vacuum spike a and pressure pulse b. However, as FIG. 5 illustrates, when there is an obstruction present, the corresponding pressure pulse is either absent, or as illustrated at c, greatly reduced. Further, any pressure pulse that may be present occurs at a relatively later point in time, and is not as clearly defined.

Figure 6:
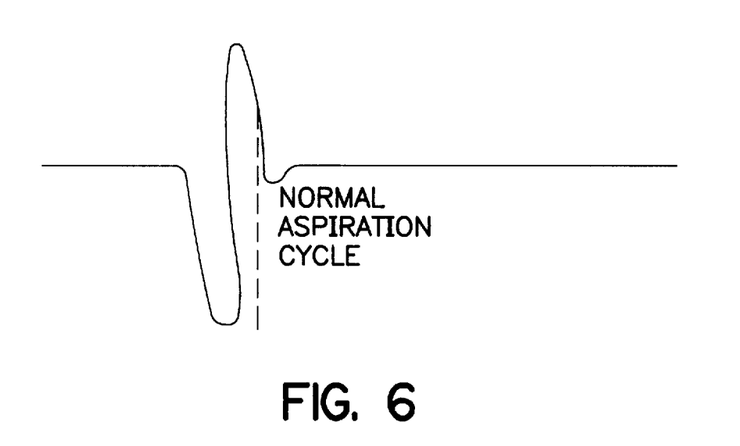
FIG. 6 is a graphical integration of the time rate of change of the pressure during a normal aspiration cycle.
Figure 7:
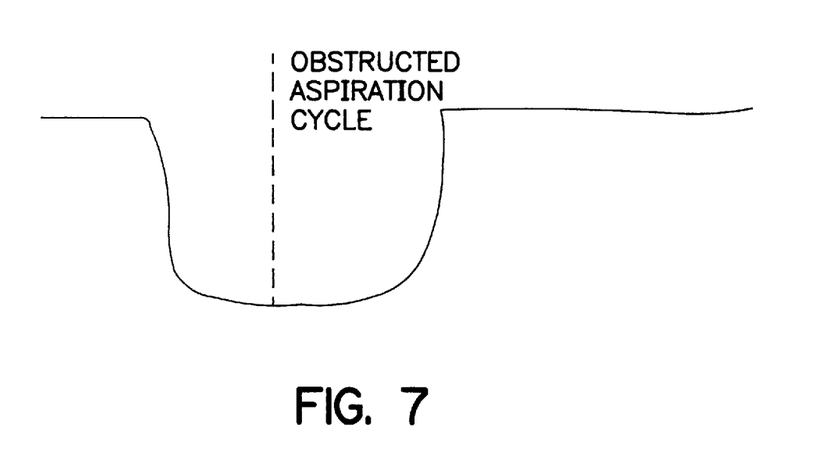
FIG. 7 is a graphical integration of the time rate of change of the pressure during an obstructed aspiration cycle.

To further differentiate between a normal aspiration cycle and one experiencing an obstruction, the time rate of change of the pressure within detector housing 32, i.e. the derivative of the actual pressure, can be electrically integrated by processor 70 to convert the signal to actual pressure. As is illustrated in FIGS. 6 and 7, the integrated signals received during a normal aspiration cycle is easily distinguishable from the integrated signal received during an obstructed aspiration cycle. Once an obstruction is detected by obstruction detector 31, processor 70 can take appropriate action.

Figure 8:
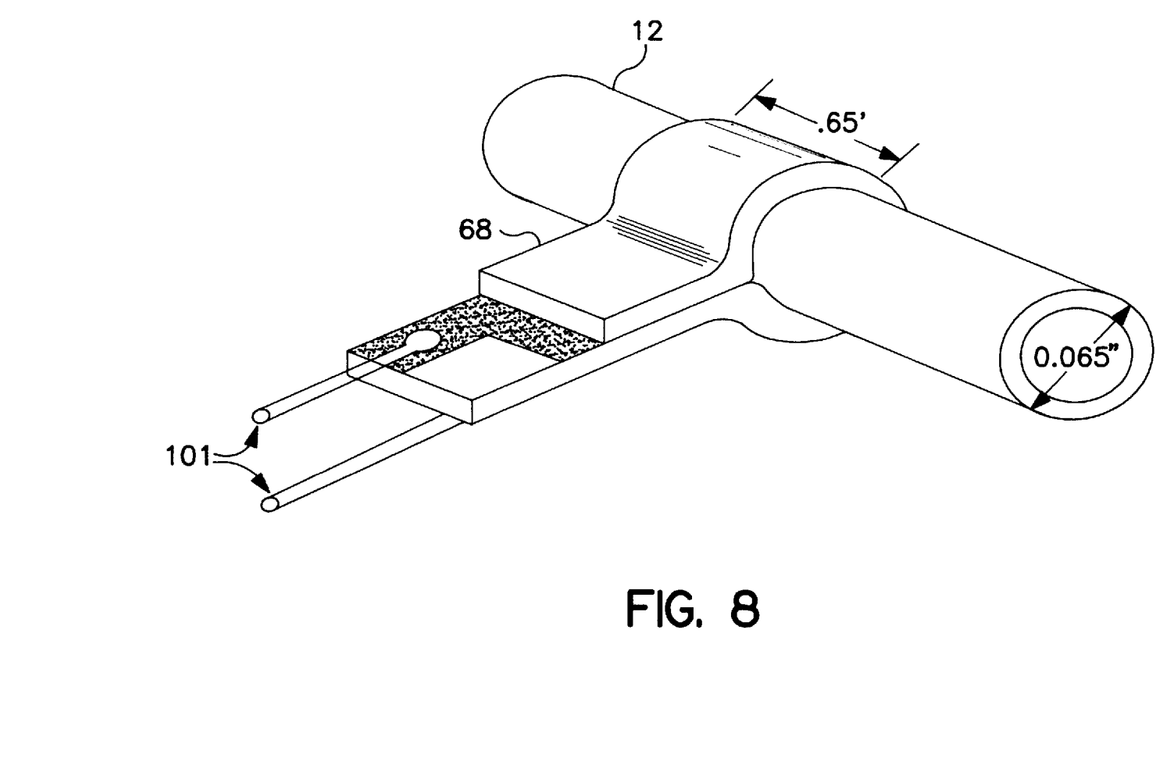
FIG. 8 is a view of a second embodiment of the present invention with tape disposed directly on the tubing.

As can be seen from FIG. 1, in the first embodiment of the present invention, a cavity is disposed at a point along tubing 12. In the second embodiment of the invention, tape can be applied to the tubing directly. As can be seen in FIG. 8, the tape, such as a film of polar poly-vinylidene fluoride (PVF) is wrapped around small gauge tubing. The PVF film, available, for example, from AMP Sensors (DTI-028K) is held in close contact with the tubing by a block conforming to the shape of the tube. An electronic circuit is provided to amplify the signal from the film.

As can be seen in FIG. 8, tubing 12 is directly surrounded by tape 68. Wires 101 are connected to tape 68. Though illustrated in FIG. 8 as wrapping around the tubing, tape 68 could also be disposed along the tubing or in another arrangement where the tape will be compressed, as will be discussed below.

Figure 9:
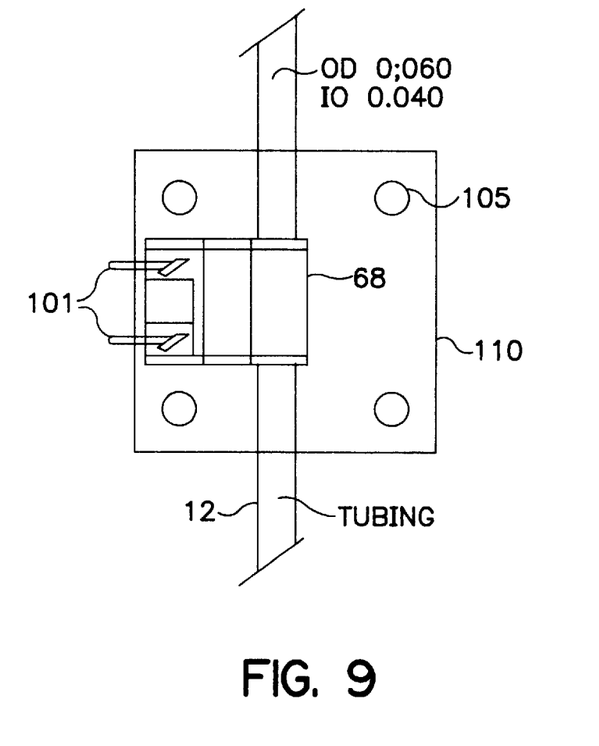
FIG. 9 is a top view of the second embodiment illustrating the tubing and tape disposed on a bottom acrylic block.
Figure 10:
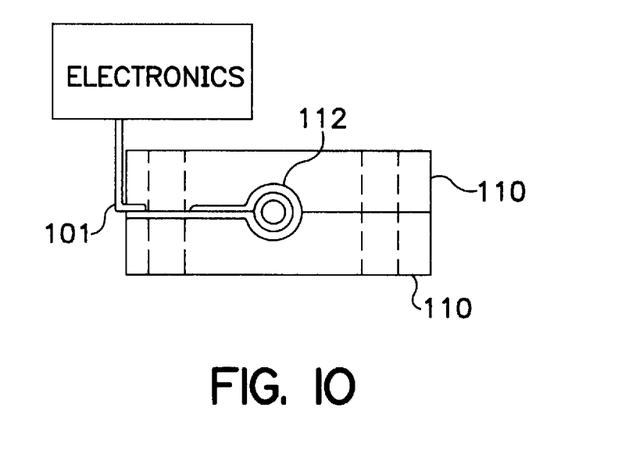
FIG. 10 is a side view illustrating the tubing and tape disposed within two blocks.

As can be seen in a top view of the device in FIG. 9, the tubing 12 with tape 68 therearound, is placed on a block 110 having holes 105. As can be seen in FIG. 10, a top block 110 is also provided. Each block has a groove 112 which corresponds to the tube 12 disposed therein.

Figure 11:
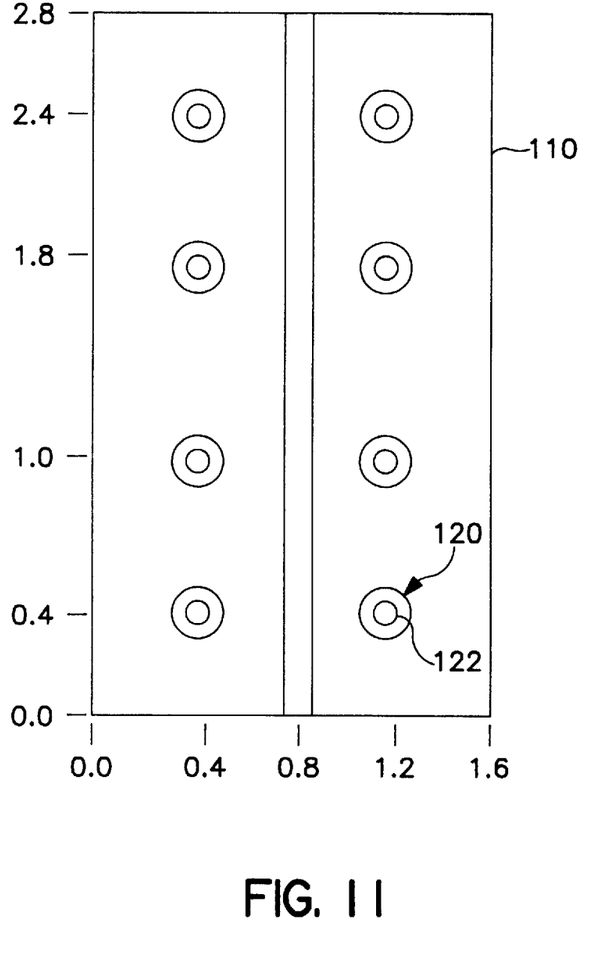
FIG. 11 is a top view of one block.
Figure 12:
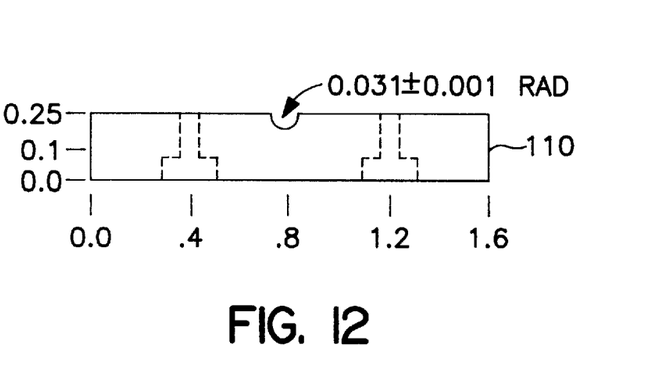
FIG. 12 is a cross sectional view of the acrylic block.

As can be seen in top and side views of the acrylic blocks 110 (FIGS. 11 and 12) holes 120 can be provided with screws 122 for securing the two blocks together. Of course other means of securing the blocks would also be contemplated. In fact, any structural arrangement for the blocks which would surround at least the portions of the tube 12 having tape 68 thereon, would be envisioned.

As the pressure in the tube increases, such as when a clot blocks a probe attached to tube 12, the walls of the tube expand. This expansion of tube 12 applies pressure to the PVF film. The film is pinched between the expanding wall of the tubing and the rigid blocks surrounding the tubing and the film. The film produces a charge in direct proportion to the rate of change of pressure within the tube. It is desirable for the change in pressure to be greater than 8 PSI per second.

Figure 13:
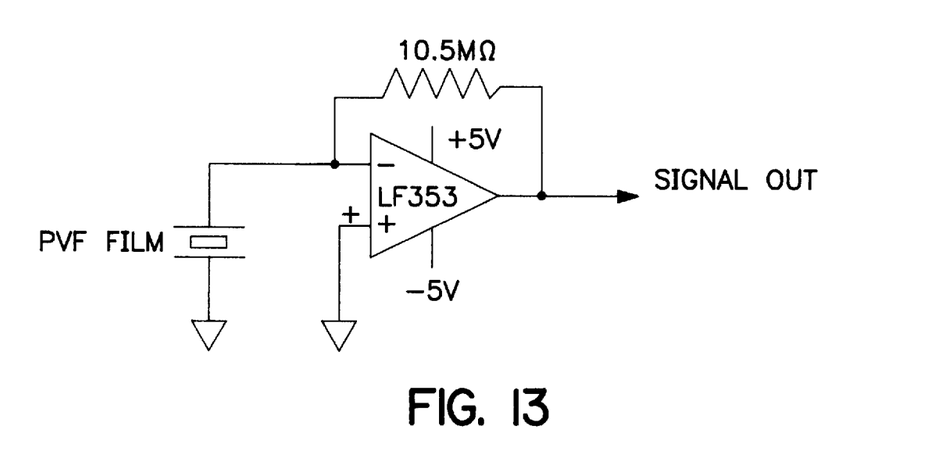
FIG. 13 is a diagram of one example of the circuitry for connection to the tape.
Figure 14:
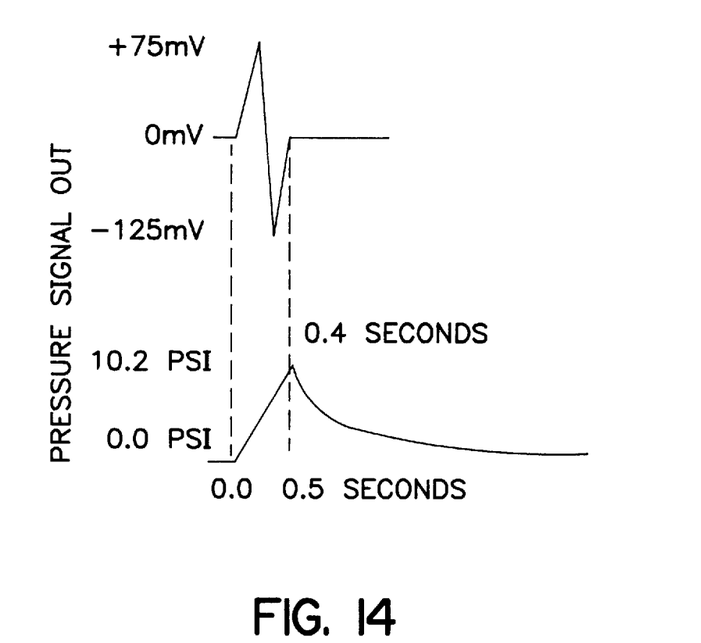
FIG. 14 is a graph of the rate of change of pressure over time.

The PVF film produces small currents (in the nano Amp range). Leakage of current between the wires of the tape will weaken and distort the signal. It is therefore desirable to use proper design techniques for the electronics due to the small currents involved. FIG. 13 illustrates one example of circuitry connected to the film. The signal of the sensor is preferably amplified so as to aid in detection of rate of changes of pressure within the tubing. FIG. 14 illustrates pressure changes over time.

The invention now being fully described, it will be apparent to one of ordinary skill in the art that any changes and modifications can be made thereto without departing from the spirit or scope of the invention as set forth herein.

What is claimed is:

1. An apparatus for detecting obstructions of a flow line, comprising:

a flow line capable of allowing fluid to flow therethrough;

a pressure detector for detecting changes in pressure within said flow line, said pressure detector disposed on said flow line or sufficiently proximate to said flow line so as to be compressed when said flow line expands; and a rigid barrier disposed proximate to said pressure detector on a side of said pressure detector opposite said flow line, said rigid barrier being sufficiently rigid so that when said flow line and pressure detector expand, said rigid barrier does not expand and said pressure detector is compressed.

2. The apparatus of claim 1, wherein said pressure detector is piezo-electric tape.

3. The apparatus as defined in claim 2, wherein said piezo-electric tape comprises polar poly-vinylidene fluoride.

4. The apparatus according to claim 1, wherein said rigid barrier is at least one block disposed proximate to said pressure detector.

5. The apparatus according to claim 4, wherein said at least one block is two blocks disposed in a face-to-face relationship, wherein each face of each block comprises a groove for said flow line.

6. The apparatus of claim 5, wherein said two blocks are made of acrylic and are held together by screws.

7. The apparatus of claim 2, wherein said piezo-electric tape produces a charge in direct proportion to the rate of change of pressure within the tube when the piezo-electric tape is compressed between the expanding wall of the flow line and the rigid barrier.

8. The apparatus according to claim 7, wherein said pressure detector is capable of detecting a rate of change of pressure of 8 PSI per second or more.

9. The apparatus according to claim 7, wherein said piezo-electric tape produces a signal when compressed, which signal is amplified.

10. The apparatus of claim 1, further comprising a probe connected at one end of said flow line.

11. The apparatus according to claim 10, further comprising an aspiration source disposed within said flow line and in fluid communication with said probe.

* * * * *